United States Patent [19]
Gugger et al.

[11] Patent Number: 6,033,714
[45] Date of Patent: *Mar. 7, 2000

[54] PROCESS FOR PRODUCTION OF ISOFLAVONE FRACTIONS FROM SOY

[75] Inventors: Eric Gugger, Latham; Richard D. Grabiel, Mt. Zion, both of Ill.

[73] Assignee: Archer Daniels Midland Company, Decatur, Ill.

[ * ] Notice: This patent is subject to a terminal disclaimer.

[21] Appl. No.: 09/035,588

[22] Filed: Mar. 5, 1998

Related U.S. Application Data

[60] Continuation-in-part of application No. 08/868,629, Jun. 4, 1997, Pat. No. 5,792,503, which is a division of application No. 08/614,545, Mar. 13, 1996, Pat. No. 5,702,752.

[51] Int. Cl.$^7$ ........................................................ A23L 1/20
[52] U.S. Cl. ........................ 426/634; 426/429; 426/431; 426/490; 426/520; 549/403
[58] Field of Search .................... 426/431, 429, 426/443, 478, 490, 492, 520, 634, 648, 425; 549/403

[56] References Cited

U.S. PATENT DOCUMENTS

| | | | |
|---|---|---|---|
| 5,679,806 | 10/1997 | Zheng et al. ............................. | 549/403 |
| 5,702,752 | 12/1997 | Gugger et al. ........................... | 426/634 |
| 5,792,503 | 8/1998 | Gugger et al. ........................... | 426/634 |

OTHER PUBLICATIONS

Academic Press, Inc.—1985—New Protein Foods, vol. 5, Seed Storage Proteins (This article was cited near the bottom of p. 1 of the specification.).

*Primary Examiner*—Milton Cano
*Attorney, Agent, or Firm*—Laff, Whitesel & Saret, Ltd.; Lisa C. Childs

[57] ABSTRACT

The temperature sensitive differential of the solubilities of various isoflavone fractions is used to initially separate the fractions by heating an aqueous soy molasses or soy whey feed stream. The temperature of the feed stream is selected according to the temperature at which a desired isoflavone fraction or fractions become soluble. Then, the heated feed stream is passed through an ultrafiltration membrane having a cutoff which further selects desired isoflavone molecules by size. In some examples, the permeate is subjected to reverse osmosis in order to concentrate the solids. The resulting permeate is put through a resin adsorption process carried out in at least one liquid chromatography column to further separate the desired isoflavone fractions. A plurality of such columns may be used to provide a continuous process. Various processes are described for drying and crystallizing the isoflavone fractions. The preferred process includes eluting the output stream from the chromatography column, evaporating the eluted stream, and then using one of the techniques of (1) spray drying, (2) centrifuging, or (3) filtering.

40 Claims, 3 Drawing Sheets

Process Flow Diagram

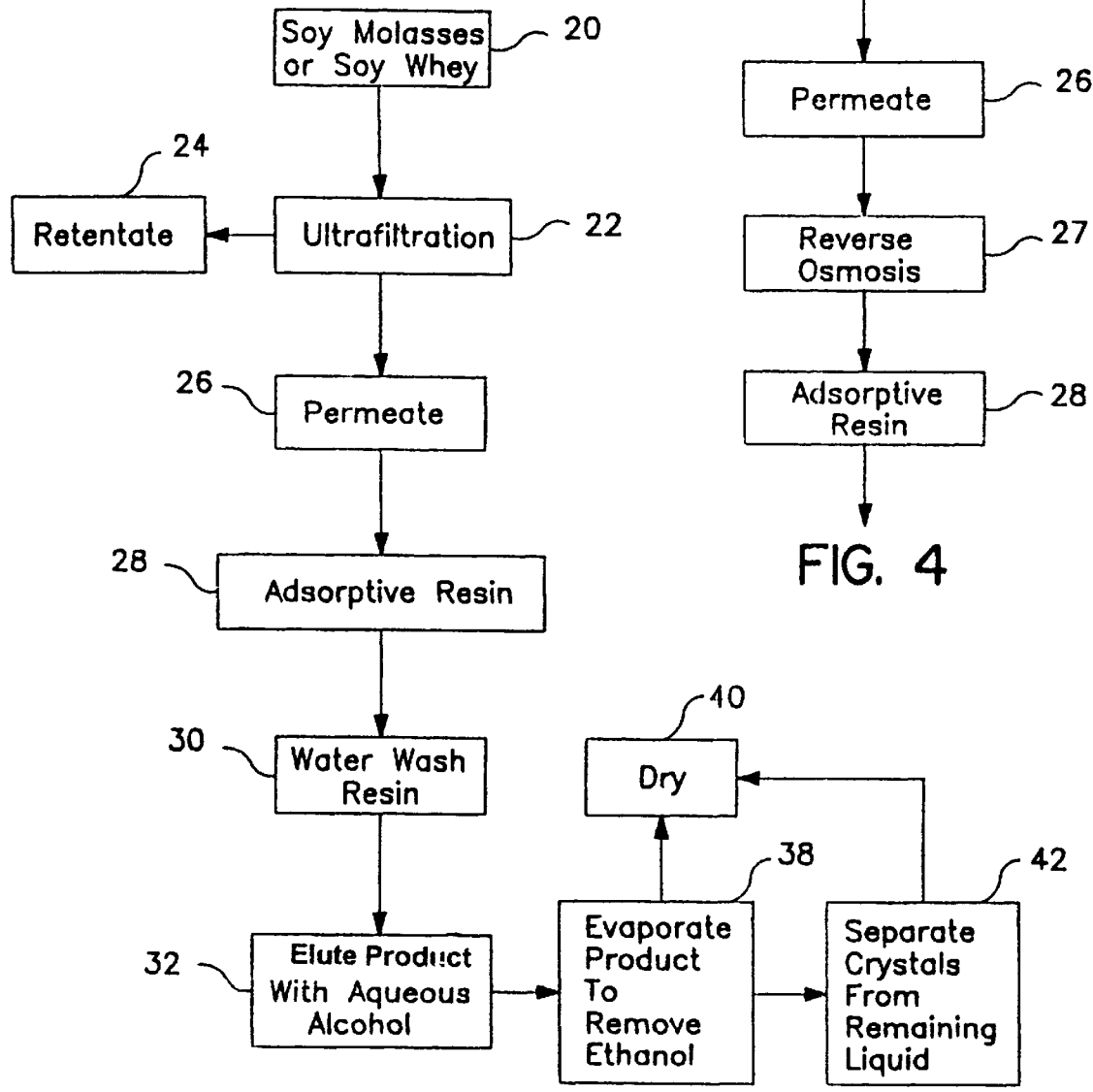

6,033,714

PROCESS FOR PRODUCTION OF ISOFLAVONE FRACTIONS FROM SOY

This is a continuation-in-part of Ser. No. 08/868,629, filed Jun. 4, 1997, now U.S. Pat. No. 5,792,503, which in turn is a division of Ser. No. 08/614,545, filed Mar. 13, 1996, now U.S. Pat. No. 5,702,752.

The invention relates to processes for producing isoflavone fractions by a treatment of an aqueous alcohol extract of defatted soybean flakes.

BACKGROUND OF THE INVENTION

This invention will find use when processing any one of a number of plants or plant material, the preferred one of which is the soybean.

Those who are skilled in the art will readily perceive a variety of other plants or plant material which may be used, for example, kudzu and subterranean clover are also expected to work in this invention. Accordingly, the terms plant, plant material, and vegetable is to be construed herein as including these and other suitable materials.

For some background information on processing soy, reference may be made to the following articles: *"Isolated Soy Protein"* by C. W. Kolar, S. H. Richert, C. D. Decker. F. H. Steinke, and R. J. VanderZanden, found as chapter VIII of *New Protein Foods,* Vol. 5, eds. Aaron M. Altschul and Harold L. Wilcke, Academic Press, Inc. 1985; *"Traditional Soyfoods: Processing and Production"* by Peter Goldbitz; and *"Soy Protein Products: Processing And Use"* by Edmund W. Lusas and Mian N. Raz, both (0022–3166/95) published 1995 by the American Institute of Nutrition. A process for producing soy whey is disclosed on pages 386, 387 of *"Soybeans Chemistry, Technology, and Utilization"* by KeShun Liu, published by Chapman & Hall, 115 Fifth Avenue, New York, N.Y. 10003.

Isoflavones are a unique class of plant flavonoids that have a limited distribution in the plant kingdom and may be physically described as colorless, crystalline ketones. The most common and important dietary source of these isoflavones are soybeans which contain the following twelve isoflavone isomers: genistein, genistin, 6"-0-malonylgenistin, 6"-0-acetylgenistin; daidzein, daidzin, 6"-0-malonyldaidzin, 6"-0-acetylgenistin; glycitein, glycitin, 6"-0-malonylglycitin, 6"-0-acetylglycitin (Kudou, Agric. Biol. Chem. 1991, 55, 2227–2233). Ninety-seven to ninety-eight percent of the soybean isoflavones are in the glycosylated form.

Traditionally, individuals have been limited in their use of soy foods to increase their levels of dietary isoflavones because the number and variety of soy foods available in the U.S. marketplace is limited. Also, natural flavors and color of some soy products have been described as bitter and unappetizing.

The isoflavone, genistin, was first isolated from soybean meal in 1931 by Walz (Justus Liebigs Ann. Chem 489, 118) and later confirmed in 1941 by Walter (J. Amer. Chem. Soc. 63, 3273). Patents have described the production of isoflavone enriched soy-protein products (WO 95/10512; WO 95/10529; WO 95/10530), genistin malonate and daidzin malonate (U.S. Pat. No. 5,141,746), pharmaceutical-type compositions containing isoflavones (U.S. Pat. Nos. 5,424,331; 4,883,788), and isolation and modification of isoflavones from tempeh (U.S. Pat. Nos. 4,390,559; 4,366,248; 4,366,082; 4,264,509; 4,232,122; 4,157,984). The present patent relates to the manufacture of highly enriched isoflavone products containing either a wide-range of soy isoflavones or highly-purified genistin gained from an ethanol extract of defatted soybean flakes.

Coronary heart disease (CHD) is a leading cause of death, especially in the United States and other industrialized nations. Elevated total and LDL cholesterol levels are important risk factors for CHD. In humans, soy protein products appear to lower serum total cholesterol levels by an average of about 9.3% and to lower low-density lipoprotein (LDL) cholesterol by an average of about 12.9% when consumed at an average intake level of 47 g soy protein per day (Anderson et al., *NEJM,* 333:276–282, 1995).

Isoflavones (Phytoestrogens) are implicated as a class of compounds in soy protein products which is at least partly responsible for this cholesterol-lowering effect in animals (Setchell, in McLachlan JA, ed., Estrogens in the Environment II:69–85, 1985). In addition, studies with primates suggest that soy isoflavones may account for up to about 60–70% of the hypocholesterolemic properties of soy protein (Anthony et al., Circulation, 90:Suppl:I-235. (abstract), 1994; Anthony et al., J. Nutr., 125:Suppl 3S:803S–804S. (abstract), 1995; Anthony et al., Circulation, 91:925. (abstract), 1995).

It has also been suggested that isoflavones have an ability to play a role in the prevention of certain cancers. Japanese women who have consumed diets rich in isoflavones appear to have a very low incidence of breast cancer (Adlercreutz et al., J. Nutr. 125:757S–770S, 1995). Soy products have also been shown to decrease mammary tumor formation or to inhibit mammary tumor progression in rat breast cancer models (Barnes et al., Clin. Biol. Res. 347:239–253; Hawrylewicz et al., J. Nutr. 121:1693–1698, 1991). Genistein has been shown to inhibit protein tyrosine kinase (Akiyama et al., J. Biol. Chem. 262:5592–5595, 1987), to inhibit angiogenesis (Fotsis et al., Proc. Natl. Acad. Sci. USA 90:2690–2694, 1993), and to induce differentiation in several malignant cell lines (Peterson, J. Nutr. 125:784S–789S, 1995), all of which may be important risk factors in cancer development. Genistein and Biochanin A also appear to inhibit the growth of androgen-dependent and independent prostatic cancer cells in vitro (Peterson and Barnes, Prostate 22:335–345, 1993). Genistein may act as an antioxidant (Wei et al., Nutr. Cancer 20: 1–12, 1993).

Beyond cancer, it is thought that at least some of the soy isoflavone fractions are especially beneficial for women in general since it is a source of plant estrogen. It is thought that plant estrogen provides many of the advantages and avoids some of the alleged disadvantages of animal estrogen. Hence, it is especially desirable to enable the isoflavone fractions to be used in a wide variety of ways, such as in beverages and foods. This means that the isoflavone fractions should not introduce unacceptable tastes or unappetizing colors.

The process described in the above-cited U.S. Pat. No. 5,702,752 produces an excellent concentration of isoflavones. However, the end product could be improved because it had a color and flavor which tended to limit its desirability. For example, there has been a tendency to think that soy isoflavone fractions should be limited to uses where the consumer does not either taste or really see it, as when the isoflavons are formed into tablets, pills, or capsules.

There are other uses for isoflavones which are desired. For example, there are times when it is desirable to use the isoflavones in foods, beverages, medical foods, and certain dietary supplement products.

SUMMARY OF THE INVENTION

Accordingly, an object of this invention is to provide isoflavone fractions which have a neutral color and a bland flavor. In particular, an object is to provide a supplement which may be included in a great variety of foods and beverages, and more particularly, an object is to provide materials where smaller quantities deliver the same amount or more of the desired isoflavones.

Another object is to provide a process that uses soy whey, which has sometimes been an unacceptable starting material for use in more important and valuable products; therefore, it is often generated as a by-product of soy processing.

In keeping with an aspect of the invention, these and other objects are accomplished by starting preferably with soy molasses, or alternatively with soy whey, which is subjected to ultra-filtration in order to produce a permeate which then passes through a column containing an adsorbing resin. The resin is then washed with water and eluted with aqueous alcohol, preferably ethanol. Next the alcohol is evaporated until the solids are in the range of approximately 1–20% of the remaining liquid. The resulting product is either dried as is, preferably by spray drying, or may be centrifuged or filtered to separate a precipitate. The precipitate is then dried by spray drying, or other appropriate drying methods.

BRIEF DESCRIPTION OF DRAWINGS

These and other objects of this invention will become more apparent from the following specification taken with the attached drawings, in which:

FIG. 3 is a process flow diagram showing the production of the inventive product; and FIG. 4 is a fragment of FIG. 3 including a reverse osmosis step.

DETAILED DESCRIPTION OF THE INVENTION

This invention employs methods based on the differential solubilities of isoflavones in aqueous solutions. Genistin is the least water soluble of the isoflavone glycosides, is insoluble in cold water, and is only slightly soluble in hot water (FIG. 1).

Figure 1:
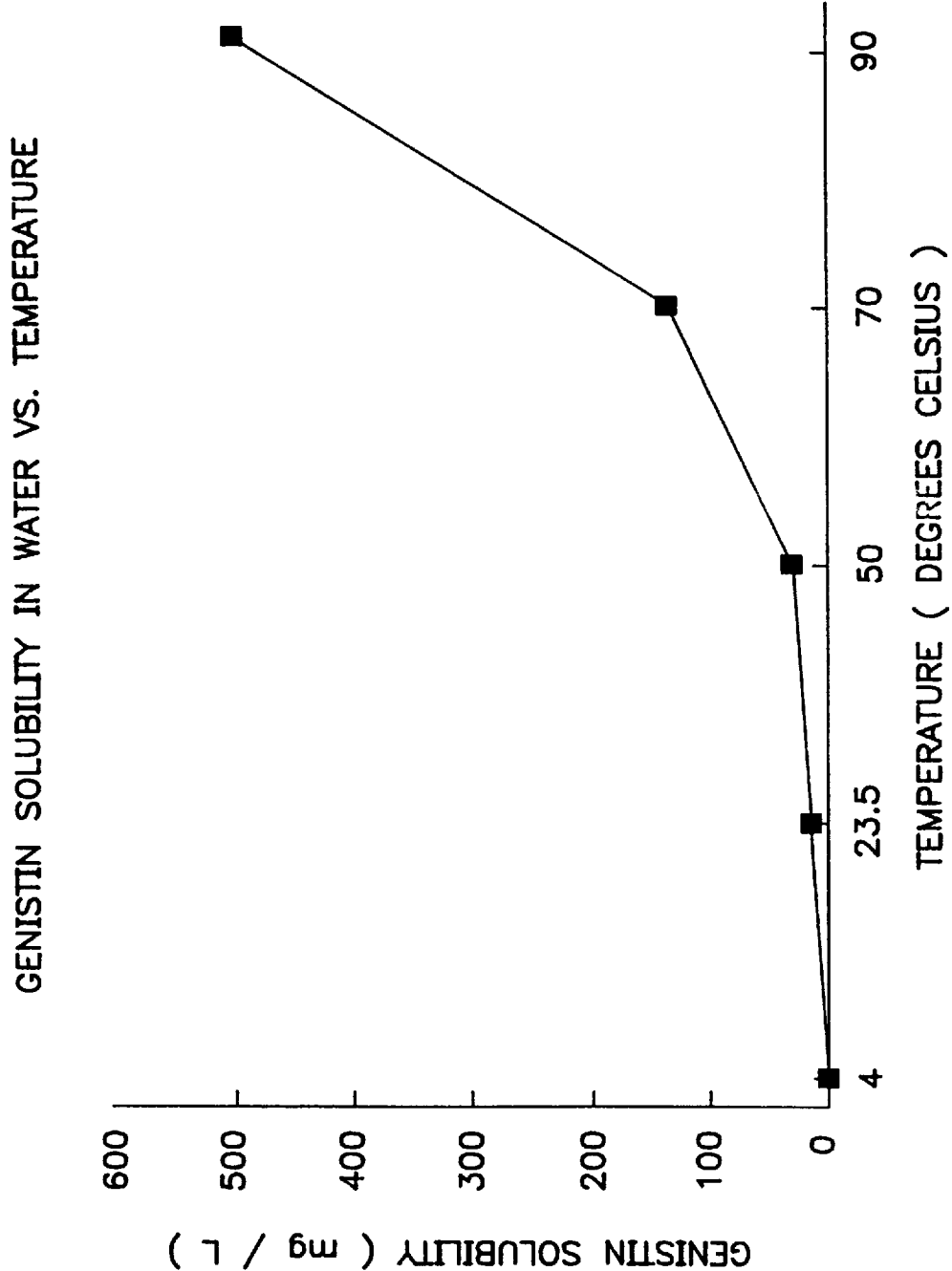
FIG. 1 is a graph showing the solubility of genistin in water vs. temperature.

In greater detail, FIG. 1 shows that the solubility of genistin is practically unchanged as the temperature increases from 4° C. to 50° C., but that the solubility increases rapidly as the temperature increases from 70° to 90° C. Therefore, if the manufacturing process is to recover genistin, the recovery step should be carried out at the high temperature end of the scale.

All isoflavone glycosides other than genistin have higher solubilities in water and readily pass through an ultrafiltration membrane, along with other water soluble components. By increasing the temperature of the aqueous solution prior to ultrafiltration, genistin and all other isoflavones can be separated from insoluble materials. The isoflavones in the ultrafiltration permeate can be recovered by treating the solution with a resin, washing the resin with water to remove soluble sugars, and eluting the isoflavones with a mixture of ethanol and water, followed by drying.

The starting material for the inventive processes is derived from an aqueous ethanol extract of hexane-defatted soybean flakes. The defatted soybean flakes are extracted with aqueous ethanol (approximately 60–80% ethanol by volume) at temperatures in the range of about 44°–63° C. or 120–150° F. This aqueous ethanol extract is then subjected to a vacuum distillation in order to remove ethanol. The alcohol-stripped extract is also known as "soy molasses" or "soy solubles." Soy molasses is a by-product of processes which make soy protein concentrate.

An alternative starting material is soy whey. The whey may be made in any of many well-known ways, one of which is shown on page 387 of the above-cited book "Soybeans" by KeShun Liu. In general, this Liu process begins with defatted soy meal which is passed through an aqueous extraction of pH 9.0. Then, the aqueous material is centrifuged followed by an isolectric precipitation at a pH 4.5. The resulting material is separated into curd and whey. The curd is further processed into soy protein isolate.

Then the extract (either molasses or whey) is adjusted within an appropriate temperature range (about 65°95° C.) and subjected to ultrafiltration preferably by using a 100,000 molecular weight cut-off (MWCO) membrane. However, the process is not limited to this 100,000 cut-off membrane since any membrane or ceramic element which enables a filtration of the desired isoflavones may be used, such as a membrane in the range of 600–1,000,000 molecular weight cut-off. The smallest cut-off membrane suitable for the inventive procedures should pass a molecular weight of about 532, which provides a sufficient retention of insoluble material and passage of isoflavones. Moreover, ultrafiltration may be performed on the basis of size, rather than molecular weight. Size, of course, often correlates roughly with molecular weight. An 0.1 micron membrane is another preferred membrane.

Figure 2:
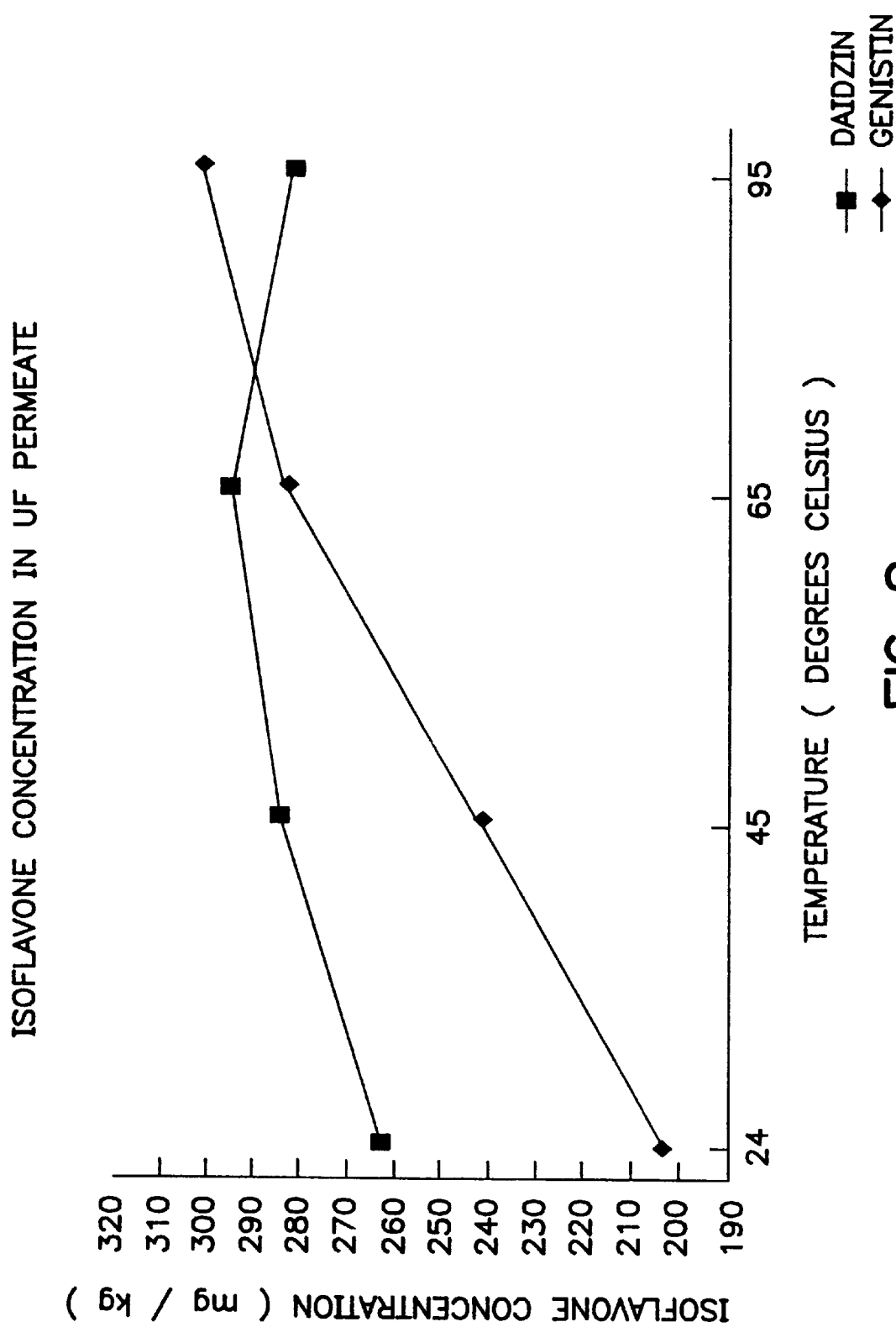
FIG. 2 is a graph showing the concentration of isoflavone in a UF permeate vs. temperature.

The effect of temperature on the concentration of two principal isoflavones, daidzin and genistin, in the UF permeate, is shown in FIG. 2. Cooler temperatures result in lower concentrations of genistin in the UF permeate. Daidzin concentrations are much less affected by temperature. To achieve optimal concentrations of isoflavones in the UF permeate, ultrafiltration should be carried out at a temperature above 65° C.

For example, FIG. 2 shows the differential between the concentration of daidzin and genistin in an aqueous solution permeate subjected to ultrafiltration. Ultrafiltration at 24° C. produces a high concentration of daidzin and a low concentration of genistin. Therefore, if the manufacturing step is to recover daidzin and reject genistin, perhaps the recovery should be carried out at the relatively low temperature of 24° C., although the exact temperature may be selected on a basis of how much genistin can be located in the permeate. On the other hand, if the manufacturing process is designed to recover both daidzin and genistin, perhaps it would be better to operate at the crossover point of about 78° C. For genistin, recovery should be carried out at a higher temperature.

A flow diagram representing one example of a manufacturing processes is shown in FIG. 3.

In greater detail, FIG. 3 shows at 20 that the preferred starting material is either soy molasses or soy whey which is subjected to ultrafiltration at 22. At 24, the retentate of the ultrafiltration is further processed, recycled, or otherwise used in another process.

If a batch type process is employed, the volume of the UF retentate fraction 24 is reduced during the ultrafiltration process by about one-third to two-thirds of the original alcohol-stripped extract volume, or stated otherwise is up to 12–15% solids. The UF retentate may be diafiltered with about one to three retentate volumes of water, which has been previously adjusted to be within a temperature range of about 65–95° C. in order to recover a greater percentage of isoflavones in the permeate. The retentate will then be used in some other process having no direct relationship with the process shown in FIG. 3.

With or without the diafiltered permeate, the ultrafiltration permeate at 26 contains a variety of isoflavones and is adjusted to an appropriate temperature (45–95° C.). Then, it is treated with an adsorptive resin at 28 in either a batch or, preferably, a chromatography column type process. As shown in FIG. 4, in some examples, a reverse osmosis step 27 may be included between the permeate step 26 and the adsorptive step 28.

More preferably, a continuous process is designed to use a plurality of chromatography columns wherein one column is loading while another column is eluting with still other columns in various stages between loading and eluting. This way, there may be a continuously flowing stream of finished product. There are a number of resins which may be used in the chromatography column. The resin may be, but is not limited to, ethylvinylbenzene-divinyl-benzene, styrene-divinyl-benzene or polystyrene polymers or copolymers, and may be either ionic or non-ionic.

A particularly attractive resin for use in the inventive process is "Amberlite" XAD-4 polymeric adsorbent sold by the Rohm and Haas Company at the Independence Mall West, Philadelphia, Pa. 19105. The manufacturer describes this resin as a non-ionic polymeric adsorbent supplied as insoluble white, cross-linked polymer beads which derives its adsorptive properties from its macroreticular structure containing both a continuous polymer phase and a continuous pore phase. This structure gives this polymeric adsorbent excellent physical, chemical, and thermal stability. "Amberlite" XAD-4 polymeric adsorbent is further described as capable of being used through repeated cycles, in columns or batch modes, to adsorb hydrophobic molecules from polar solvents or volatile organic compounds from vapor streams. Its characteristic pore size distribution is said to make "Amberlite" XAD-4 polymeric adsorbent a choice for the adsorption of organic substances of relatively low molecular weight.

The physical properties of "Amberlite" XAD-4 are described by this manufacturer as follows:

| | |
|---|---|
| Matrix | Macroreticular cross-linked aromatic polymer |
| Appearance | White translucent beads |
| Particle Size | 0.3–1.2 mm (90% within) |
| True Wet Density | 1.02 g/ml |
| Surface Area | 800 m$^2$/g minimum |
| Porosity | 55% (vol/vol) minimum |
| Pore Size Range | 1–150A |

Following passage through the chromatography columns, the resin is washed with water at 30. Next, the isoflavones are eluted at 32 with an aqueous alcohol, such as ethanol, methanol, or isopropanol (20–100% by volume, at 25–85° C.) as either a gradient or single percentage process. Here, 80% ethanol is preferred at a temperature of 40–70° c.

At 38, the resulting material is evaporated to provide a liquid having about 1–20% dry solid material in order to begin crystallization by removing the alcohol used in step 32. The evaporated product-may then be further processed by spray drying at 40. The resulting dried material is approximately reddish-brown and approximately 20–60% isoflavones on a solids basis. It is thought that the most usual range for such dried material produced from soy molasses is about 30–50% isoflavones and from soy whey is about 20–40% isoflavones which seems to depend on the Isoflavone concentration in the starting material, feed loading, and other variables. Or, further processing may be carried out by adjusting the evaporated product to an appropriate temperature (4–45° C.) to promote crystallization of Isoflavone fractions.

These crystals can be then be separated by settling, decanting, centrifuging or filtering crystals at 42, to produce the resulting product which is cream colored, bland tasting, and about 50–90% isoflavones upon drying. It is thought that decanting, centrifugal filtration or using Hydroclone® machinery available from Dorr-Oliver will also work for such separation. When produced from soy molasses the resulting crystalline product is most usually 80–90% isoflavones and when produced from soy whey, is most usually 55–70% isoflavones.

EXAMPLES

1) Ultrafiltration of Soy Solubles

Using a stainless steel steam-heated immersion coil, soy solubles (15.26 kg) were heated to a constant temperature of about 80° C. The soy solubles were then passed through a model 92-HFK-131-UYU spiral wound, polysulfone, 10,000 nominal molecular weight cut-off ultrafiltration membrane (Koch Membrane Systems, Inc., St. Charles, Ill.) by using a peristaltic pump. Back pressure on the exit side of the membrane was adjusted by means of a hand-tightened clamp to provide a permeate flow of 70 ml/minute. Ultrafiltration was continued until 9.4 kg of permeate was collected leaving 4.8 kg of retentate. Isoflavone profiles of the various fractions are shown below:

| Sample | Weight (kg) | % Solids | Total Isoflavones (g) | Genistin (g) | Daidzin (g) |
|---|---|---|---|---|---|
| Solubles | 15.26 | 8.65 | 11.45 | 4.01 | 4.30 |
| Retentate | 4.8 | 11.5 | 4.63 | 1.75 | 1.67 |
| Permeate | 9.4 | 7.7 | 6.6 | 2.29 | 2.68 |

2) Diafiltration of UF Retentate

Ultrafiltration retentate (80° C. initial temperature) was subjected to ultrafiltration as described in Example 1, except that 4.8 kg of tap water (25° C.) was fed into the retentate at a feed rate which is the same as the permeate rate or flux of the permeate that was being produced. The retentate was then further ultrafiltered to a final weight of 1.93 kg. Isoflavone profiles of the various fractions is shown below:

| Sample | Weight (kg) | % Solids | Total Isoflavones (g) | Genistin (g) | Daidzin (g) |
|---|---|---|---|---|---|
| Retentate | 4.8 | 11.5 | 4.63 | 1.75 | 1.67 |
| Diafilt. Permeate | 7.25 | 4.28 | 2.12 | 0.72 | 0.96 |
| Diafilt. Retentate | 1.93 | 12.26 | 2.14 | 0.91 | 0.58 |

3) Adsorption and Recovery of Isoflavones From a Resin

A glass liquid-chromatography column (2.54 cm i.d.) was slurry packed in 70% ethanol with Dow XUS 40323 divinyl-benzene, ethylvinylbenzene copolymer resin. The resin was cleaned with an additional 500 mL of 70% wt ethanol followed by 0.1% wt NaOH (500 mL) and water (500 mL). The resin was then back-flushed with water until the resin bed volume had expanded by about one half of its originally packed volume in order to partition the resin by size. The final packed volume was 100 mL. Fresh UF permeate (2000 mL or 20 column volumes) at an initial temperature of 60° C. was fed through the resin bed at 6 column volumes/hour or 10 mL/minute. The resin bed was washed with 500 mL of water at 10 mL/minute to remove residual sugars and other impurities. Isoflavones were then eluted from the resin with a linear gradient of 20–95% ethanol (500 mL total) at 10 mL/minute. Next, the entire ethanolic isoflavone containing fraction was vacuum dried to obtain a product with the following profile:

| Sample | Weight (g) | Total Isoflavones (g) | Genistin (g) | Daidzin (g) |
|---|---|---|---|---|
| Column Product | 6.56 | 2.2 | 0.92 | 0.83 |

4) Elimination of Undesirable Taste And Color

The process described in U.S. Pat. No. 5,679,806 results in a product which is enriched in isoflavone fractions at a concentration of 30–50% on a dry basis. This product has a reddish-brown color and has a bitter flavor. Although its high isoflavone content makes it a desirable product for many applications, its color and flavor may preclude its use in certain types of products where sensory attributes are important, such as foods and beverages.

This example produces a product which is lighter in color and bland in flavor, with a higher isoflavone concentration which occurs upon removal of the color and flavor components. The new product produced by this example also has an increased utility because smaller quantities of the starting material is required to deliver approximately the same amount of isoflavones. Also, the improvement in flavor and color enables a use of the isoflavones in a wide variety of applications, such as foods, beverages, medical foods, and certain dietary supplement products.

Soy solubles ultrafiltered at 22 produce a permeate having approximately 1–20% solids. This leads to a drying end step that may be carried out by any suitable means, the preferred means being spray drying.

More particularly, at 28, this permeate was passed through a liquid chromatography column containing a polystyrene divinyl-benzene resin ("Amberlite-XAD-4") to adsorb isoflavones. Thereafter, at 30, the resin was washed with water. Then, the isoflavones were eluted from the resin at 32 with aqueous ethanol (in the range of 20–100% of alcohol and preferably about 70% ethanol). Next, the ethanol was evaporated at stage 38 to about 1.098% solids in order to produce a feed to a dryer at 40. In this example, the evaporator was heated by direct steam injection. While any of many types of dryers may be used, preferably a spray dryer is used at 40.

However, with this example, instead of completion of spray drying after elution step 32, the product was treated in the following manner:

19.29 kg of spray drier feed, containing a visible amount of precipitated material, was evaporated under vacuum in order to remove water and increase solids content. 200 g samples were taken both prior ("Spray Dryer Feed") and during ("Concentrate 1" and "Concentrate 2") evaporation in order to monitor the effect of solids content on the isoflavone recovery. These samples were allowed to cool to room temperature (about 20° C.) and subsequently centrifuged at 900×G for about 5 minutes in order to sediment the precipitate. The resulting supernatant was poured off of the sedimented precipitate and then the precipitate was dried at 140° F. (60° C.) for 16 hours. Next, all samples were analyzed for isoflavone content by HPLC, and were found to be a light cream color and to have a bland taste.

The recovery of isoflavones during the test carried out in this example are set forth in the following tables. Table I gives the isoflavone recovery during a processing of three samples designated A–C. The samples designated A were taken from a spray dryer feed, samples B (concentration I) were taken from the evaporator at step 38 during an early stage of the evaporation, and samples C (concentration II) were taken from the evaporator during a later stage of the evaporation. For each of the samples, the tests were run, respectively, on a complete dryer feedstream (A), upon a supernatant which was poured off after decanting (B), and upon the precipitate (C).

The solids prior to centrifugation and the amounts of isoflavones that were recovered are set forth in Table II. The breakdown of the isoflavones that were recovered are set forth in Table III. The conclusion is that each of the tests shows results that are attractive for certain uses. Therefore, the practitioner will select the particular process which best reflects the results that he seeks.

TABLE I

| Sample | % Solids (Soy Whey) | Isoflavones ppm | Weight (g) | Total Isoflavones |
|---|---|---|---|---|
| A Spray Dryer Feed | 1.098 | 5583.4 | 200.04 | 1.117 |
| A Spray Dryer Feed Supernatant | 0.848 | 2937.6 | 192.04 | 0.564 |
| A Dried Spray Dryer Feed Precipitate | 100.00 | 849624.8 | 0.56 | 0.477 |
| B Concentrate I | 1.814 | 9313.5 | 200.01 | 1.863 |
| B Concentrate I Supernatant | 1.308 | 3980.8 | 185.35 | 0.738 |
| B Dried Concentrate I Precipitate | 100.0 | 891696.8 | 1.21 | 1.077 |
| C Concentrate II | 4.633 | 23404.6 | 200.00 | 4.681 |
| C Concentrate II Supernatant | 3.173 | 8712.9 | 170.72 | 1.487 |
| C Dried Concentrate II Precipitate | 100.0 | 838399.3 | 3.65 | 3.057 |

TABLE II

| % Solids Prior to Centrifugation | % Recovery of Isoflavones in Centrifuged Precipitate |
|---|---|
| 1.098(A) | 49.49 |
| 1.814(B) | 60.39 |
| 4.633(C) | 68.22 |

TABLE III

| Isoflavone | Dried Spray Dryer Feed Precipitate (ppm) A | Dried Concentrate I Precipitate (ppm) B | Dried Concentrate II Precipitate (ppm) C |
|---|---|---|---|
| Daidzin | 347109.3187 | 422936.0742 | 412219.9703 |
| Glycitin | 37066.4070 | 43523.2763 | 44077.5906 |
| Genistin | 408166.8156 | 357561.8669 | 305240.8582 |
| Malonyl-Daidzin | 4195.0096 | 6128.8092 | 7556.7644 |
| Malonyl-Glycitin | 67.4223 | 96.0281 | 157.1695 |
| Acetyl-Daidzin | 26792.2537 | 32540.1269 | 35771.3900 |
| Acetyl-Glycitin | 389.8314 | 794.5519 | 1522.1046 |
| Malonyl-Genistin | 1755.5026 | 2469.0077 | 3581.2460 |
| Daidzein | 2952.0643 | 3814.0725 | 3615.3280 |
| Acetyl-Genistin | 18471.3792 | 19019.5539 | 21794.8883 |
| Glycitein | 1031.0817 | 1039.2615 | 1154.3133 |
| Genistein | 1627.7324 | 1774.1731 | 1707.7167 |
| Total ppm (%) | 849624.8 (85.0%) | 891696.8 (89.2%) | 838399.3 (83.8%) |

7) Soy Whey Starting Material

The starting material for these examples is soy whey. Soy whey is defined as a liquid from the isoelectric or the divalent cation precipitation of the solubilized fraction from the processing of soybeans into soyfoods.

Example A

Process Outline:
SOY WHEY (FIG. 3 at 20) → ULTRAFILTRATION (100,000 Mol. Wt. cut-off) (FIG. 3 at 22) → PERMEATE (FIG. 3 at 26) → REVERSE OSMOSIS (concentration) (FIG. 4 at 27) → ADSORPTIVE RESIN (FIG. 3 at 28 → WATER WASH RESIN (FIG. 3 at 30) → ELUTE PRODUCT WITH AQUEOUS ALCOHOL (FIG. 3 at 32)

Adsorption and Recovery of Isoflavones From a Resin Utilizing Soy Whey As a Starting Material, Raw Material and End Product Description:

| Sample | Total Wt. (kg) | Total Isoflavones (g) | Isoflavone Conc. (%) |
|---|---|---|---|
| Reverse Osmosis Concentrate (ROC) | 882.49 | 219.74 | 0.0249 |
| Isoflavone Concentrate Product | 0.4223 | 155.17 | 36.744 |

A plurality of 1800 ml stainless steel liquid chromatography columns were slurry packed with "Amberlite" XAD-4 divinyl-benzene copolymer polymeric absorbent resin. The resin was cleaned repeatedly with 80% wt. ethanol, water and 0.1–0.3% wt. NaOH solution. The final bed volume (BV) of resin in each column was 1500 ml.

The reverse osmosis concentrate (ROC) was heated to a temperature of 80° C. Two columns ($2 \times BV = BV2$) were fed in series at 600 ml/min. and received a total of 36 liters (12 BV2) of ROC. Individual columns then received a 60° C. water wash at 100 ml/min. (3000 ml. or 2 BV) to remove residual sugars and other impurities. Isoflavones were then eluted from the washed columns with 60° C., 80% wt. ethanol at 90 ml/min. (5400 ml or 3.6 BV) producing an ethanolic isoflavone fraction. The ethanol was evaporated and removed from the isoflavone fraction. The isoflavone fraction was then spray dried, resulting in a total of 422.3 g of a 36.745% isoflavone powder.

Example B:

Process Outline:
SOY WHEY (FIG. 3 at 20) → ULTRAFILTRATION (100,000 Mol. Wt. cut-off) (FIG. 3 at 22) → PERMEATE (FIG. 3 at 26) → REVERSE OSMOSIS (concentration) (FIG. 4 at 27) → ADSORPTIVE RESIN (FIG. 3 at 28) → WATER WASH RESIN (FIG. 3 at 30) → ELUTE PRODUCT WITH AQUEOUS ALCOHOL (FIG. 3 at 32) → EVAPORATE AQUEOUS ETHANOL (produce aqueous isoflavone solution) (FIG. 3 at 38) → AQUEOUS ISOFLAVONE SOLUTION UTILIZATION →
1) DRY AQUEOUS ISOFLAVONE SOLUTION (FIG. 3 at 40) → PRODUCT #1, or
2) COOL AQUEOUS ISOFLAVONE SOLUTION → CENTRIFUGE AQUEOUS ISOFLAVONE SOLUTION (isolate crystals) (FIG. 3 at 42) → DRY CRYSTALS (FIG. 3, at 40) → PRODUCT #2

Absorption and Recovery of Isoflavones From a Resin Utilizing Soy Whey As a Starting Material. Raw Material and End Product Descriptions:

| Sample | Total Wt. (kg) | Total Solids (%) | Total Isoflavones (g) | Isoflavone Conc. (%) |
|---|---|---|---|---|
| Reverse Osmosis Concentrate (ROC) from soy whey | 646.65 | 3.24 | 221.80 | 0.0343 |
| Isoflavone Fraction #1 | 7.73 | 4.62 | 72.03 | 0.9318 |

A plurality of 1800 ml stainless steel liquid chromatography columns were slurry packed with "Amberlite" XAD-4 divinyl-benzene copolymer polymeric absorbent resin. The resin was cleaned repeatedly with 80% wt. ethanol, water and 0.1–0.3% wt. NaOH solution. The final bed volume (BV) of resin in each column was 1500 ml.

The reverse osmosis concentrate (ROC) was heated to a temperature of 80° C. Each column received 36 L (24 BV) of ROC at 225 ml/min. Individual columns then received a 60° C. water wash at 100 ml/min. (4000 ml. or 2.7 BV) to remove residual sugars and other impurities. Isoflavones were then eluted from the washed columns with 60° C., 60% wt. ethanol at 90 ml/min. (7200 ml or 4.8 BV) producing an ethanolic isoflavone fraction. This sequence was repeated until a total of 654 L of ROC had been fed through the columns with the absorbed isoflavones then recovered in the ethanolic fraction. The ethanol was evaporated and removed, producing isoflavone fraction #1. Fraction #1 had two possibilities for utilization: 1) drying fraction #1 to produce Product #1, or 2) to be used as a raw material to recover isoflavone crystals to produce a higher % wt. isoflavone, Product #2.

Recovery of Isoflavones from the Concentrated Column Effluent (Fraction #1):

The isoflavone fraction #1 was cooled over a 2 hour period to a temperature of 25° C. resulting in isoflavone crystal formation. A sample of the cooled isoflavone fraction #1 was then centrifuged at 900×G for 10 min. to pellet the isoflavone crystals. Next, the supernatant was poured off. The remaining pellets were vacuum dried (140° F., 16 hours) and analyzed for isoflavone content. Further purification of the pellets can be obtained by water washing and repeated centrifugation.

| Sample | Weight (g) | Total Isoflavones (g) | Isoflavones (%) |
| --- | --- | --- | --- |
| Isoflavone Product #1 (Isoflavone fraction #1 on a dry weight basis) | 357.13 | 72.03 | 20.2 |
| Isoflavone Product #2 | 3.02 | 2.05 | 67.9 |

The process that is described herein has the advantage of utilizing another common soy processing by-product, soy whey, as a starting material for the manufacture of Isoflavone concentrates. When soy whey is used as the starting material, products produced from drying the concentrated column effluent can be approximately 20–40% wt., and preferably in the upper part of the range or 35–40% wt. isoflavone fractions. These products are reddish-brown in color and bitter in flavor. The high isoflavone content makes it useful for applications such as tableting and inclusion into some foods. However, where sensory attributes are important, further processing of the concentrated column effluent material can be done to produce isoflavone concentrates more suited to food and beverage additions.

Concentrated column effluents from the processing of soy whey and soy molasses can be centrifuged or filtered and then dried to produce a new isoflavone concentrate product. The new product is lighter in color, has a less bitter taste and is higher in isoflavone concentration. These improvements allow for a wider range of uses of soy whey and molasses in foods, beverages, medical foods and dietary supplements where sensory attributes are more of a concern.

Those who are skilled in the art will readily perceive how to modify the invention. Therefore, the appended claims are to be construed to cover all equivalent structures which fall within the true scope and spirit of the invention.

We claim:

1. A process for separating isoflavone fractions in an aqueous plant starting material, said process comprising the steps of:
   (a) heating an aqueous plant starting material to a constant temperature selected on a basis of an aqueous solubility for at least one desired isoflavone fraction that is to be recovered;
   (b) passing the heated starting material of step (a) through an ultrafiltration membrane to obtain a permeate, the membrane having a cut-off which passes said at least one isoflavone fraction;
   (c) treating the permeate with an adsorptive material;
   (d) washing the material of step (c) in water;
   (e) eluting said at least one adsorbed isoflavone fraction from the water-washed adsorptive material of step (d) with aqueous alcohol;
   (f) evaporating the aqueous alcohol from a stream used during the elution of step (e) in order to promote the crystallization of said at least one isoflavone fraction; and
   (g) separating the crystallized at least one isoflavone fraction from the stream of step (f).

2. The process of claim 1 wherein step (g) includes a process selected from a group consisting of decanting, hydrocloning, centrifuging and filtering.

3. The process of claim 1 wherein step (g) includes a process selected from a group consisting decanting, centrifuging, and filtering.

4. A process for separating isoflavone fractions in an aqueous plant starting material, said process comprising the steps of:
   (a) heating an aqueous plant starting material to a constant temperature selected on a basis of an aqueous solubility for at least one desired isoflavone fraction that is to be recovered;
   (b) passing the heated starting material of step (a) through an ultrafiltration membrane to obtain a permeate, the membrane having a cut-off which passes said at least one isoflavone fraction;
   (c) treating the permeate with an adsorptive material;
   (d) washing the material of step (c) with water;
   (e) eluting said at least one adsorbed isoflavone fraction from the water-washed adsorptive material of step (d) with aqueous alcohol;
   (f) evaporating the aqueous alcohol from a stream used during the elution of step (e) in order to increase the solid basis of said at least one isoflavone fraction; and
   (g) drying the at least one isoflavone fraction in the stream of step (f).

5. The process of claim 1 wherein said separation of step (g) comprises the step of centrifuging the evaporated liquid of step (f).

6. The process of claim 1 wherein said separation of step (g) comprises the step of filtering crystals from the evaporated liquid of step (f).

7. The process of claim 4, wherein step (g) is carried out by spray drying.

8. The process of either claim 1 or 4 wherein the starting material of step (a) is selected from a group consisting of soy molasses and soy whey.

9. The process of either claim 1 or 4 wherein the evaporation of step (f) was carried out at an elevated temperature.

10. The process of claim 1 wherein the at least one isoflavone fraction separated in step (g) is a light cream color.

11. The process of claim 1 wherein the isoflavone fraction separated in step (g) has a bland taste.

12. The process of either claim 1 or 4 wherein there are a plurality of isoflavone fractions recovered in step (a) and further processed in steps (b through g).

13. The process of either claim 1 or 4 wherein the process is a continuous process further comprising the steps (c), (d), and (e) comprise the sub-steps of:
   (c1) providing a plurality of liquid chromatography columns, each of which is filled with an adsorptive resin; and
   (c2) switching the permeate of step (b) and washing the adsorptive resin of step (c) so that at least one of said plurality of columns is loading while at least one other of said plurality of columns is washing; and
   (d1, e1) switching the water-wash of the step (d) and the eluting step (e) so that at least one of said plurality of columns is washing while at least one other of said plurality of columns is eluting.

14. The process of either claim 1 or 4 wherein said adsorptive material of step (c) is a styrene divinyl-benzene copolymer.

15. The process of either claim 1 or 4 wherein said adsorptive material of step (c) is a resin selected from a group consisting of either ionic or non-ionic resin.

16. The process of either claim 1 or 4 is selected from a group consisting of ethylvinylbenzene-divinyl-benzene, styrene-divinyl-benzene copolymers and polystyrene polymers.

17. The process of claim 1 wherein said step (g) is carried out by sedimenting a liquid obtained from step (f), decanting off a resulting supernatant, and processing the sedimented precipitate.

18. The process of claim 4 wherein the stream from step (f) contains a visible amount of precipitated material.

19. A process for the production of isoflavone fractions from plant matter, said process comprising the steps of:
   (a) obtaining a starting material by heating an aqueous stream including water soluble plant material to produce a stream containing a compound selected from a group consisting of soy molasses and soy whey, said heat being a temperature selected to solubilize a plurality of isoflavone fractions in said stream;
   (b) ultrafiltering the stream resulting from step (a), said filtration being carried out by a membrane having a cut off which produces a permeate stream containing said plurality of isoflavone fractions solubilized in step (a);
   (c) processing said permeate stream from step (b) by first adsorbing with an absorbing resin at least some of said solubilized isoflavone fractions and then washing said adsorption resin with water to remove residual sugars and other water-soluble impurities;
   (d) eluting said water-washed adsorption resins resulting from step (c) with an aqueous alcohol; and
   (e) evaporating an eluted stream resulting from step (d) in order to remove said aqueous alcohol therefrom to produce a stream which is approximately 1–20% solids.

20. The process of claim 19 wherein said evaporation step (e) is followed by a process selected from a group consisting of settling, centrifuging, and filtering.

21. The process of claim 19 wherein said evaporation step (e) is followed by drying.

22. The process of claim 19 wherein said adsorption resin of step (c) is carried out in a plurality of liquid chromatography columns packed with a resin selected from a group consisting of ionic ethylvinylbenzene-divinyl-benzene co polymer, non-ionic ethylvinylbenzene-divinyl-benzene co polymer, ionic styrene-divinyl-benzene co polymer, non-ionic styrene-divinyl-benzene copolymer, ionic polystyrene, and non-ionic polystyrene.

23. The process of claim 22 wherein said selected resin is a polystyrene-divinyl-benzene copolymer.

24. The process of claim 19 wherein the temperature of the heat in step (a) is in the order of about 65–95° C.

25. The process of claim 19 wherein said membrane used in said ultrafiltration of step (b) has a nominal molecular weight cut-off range of about 600–1,000,000.

26. The process of claim 24 wherein said membrane used in said ultrafiltration of step (b) has a nominal molecular weight cut-off range of 100,000 nominal molecular weight.

27. The process of claim 22 wherein said adsorbing process of step (c) is a continuous process using a plurality of liquid chromatography columns wherein at least one of said plurality of liquid chromatography columns is loading while another at least one of said columns is washing while still another of said at least one of said columns is eluting of step (d).

28. The process of claim 19 wherein said evaporated stream of step (e) is cooled to approximately 4 to 45° C. and includes centrifugation at about 900×g.

29. The process of claim 20 wherein the concentration is by said centrifuging and drying and has the characteristics set forth in Tables I, II, and III.

30. A process for extracting isoflavone enriched fractions from soy, comprising the steps of:
   (a) obtaining an isoflavone containing starting material of soy whey and heating said starting material to a temperature which solubilizes at least one isoflavone fraction;
   (b) ultrafiltering said heated starting material to produce a permeate;
   (c) subjecting said permeate of step (b) to reverse osmosis in order to concentrate said isoflavone fraction;
   (d) adsorbing said concentrate of step (c) in a liquid chromatography column containing an adsorptive resin;
   (e) washing said chromatography column with water; and
   (f) eluting the water-washed resin of step (e) with aqueous alcohol.

31. The process of claim 30 wherein the ultrafiltering of step (b) is carried out by a membrane having 100,000 molecular weight cut-off.

32. The process of claim 31 wherein said liquid chromatography columns of step (d) are packed with divinyl-benzene copolymer adsorbent resin.

33. The process of claim 32 wherein the adsorbing of the reverse osmosis concentrate of step (c) is carried out at approximately 65–95° C.

34. The process of claim 32 wherein the elution of step (f) is carried out at approximately 40–70° C. with aqueous ethanol.

35. The process of claim 32 and the further steps of:
   (g) evaporating the aqueous alcohol of step (f) in order to produce an aqueous Isoflavone mixture; and
   (h) concentrating the mixture of step (g) to produce a first end product.

36. The process of claim 32 and the further steps of:
   (g) cooling the aqueous isoflavone mixture of step (f); and
   (h) centrifuging the mixture cooled in step (g) to produce isolated isoflavone crystals.

37. The process of claim 32 wherein said reverse osmosis concentrate of step (c) has an isoflavone fraction concentration in a range of about 0.01–0.1% wt.

38. The process of claim 35 wherein the end product of said process has an isoflavone fraction concentration of approximately 20–40% weight on a dry weight basis.

39. The process of claim 36 wherein the end product of said process has an isoflavone fraction concentration in an opportunity range of 55–70% weight on a dry weight basis.

40. A product made by the process of any one of the claims 1, 4, 19 and 30.

* * * * *